(12) United States Patent
Knöpfle et al.

(10) Patent No.: US 11,304,736 B2
(45) Date of Patent: Apr. 19, 2022

(54) RIB PLATE AND RIB PLATE SYSTEM

(71) Applicant: Stryker European Operations Holdings LLC, Kalamazoo, MI (US)

(72) Inventors: Christian Knöpfle, Donaueschingen (DE); Viktor Kraft, Freiburg (DE); Jochen Fink, Schallstadt (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 99 days.

(21) Appl. No.: 16/890,412

(22) Filed: Jun. 2, 2020

(65) Prior Publication Data

US 2020/0375641 A1 Dec. 3, 2020

(30) Foreign Application Priority Data

Jun. 3, 2019 (EP) ..................... 19177888

(51) Int. Cl.
*A61B 17/80* (2006.01)

(52) U.S. Cl.
CPC ........ *A61B 17/8076* (2013.01); *A61B 17/808* (2013.01); *A61B 17/8085* (2013.01)

(58) Field of Classification Search
CPC . A61B 17/80; A61B 17/8061; A61B 17/8076; A61B 17/808; A61B 17/8085
See application file for complete search history.

(56) References Cited

U.S. PATENT DOCUMENTS

| | | |
|---|---|---|
| 6,786,909 B1 | 9/2004 | Dransfeld et al. |
| 6,960,211 B1 | 11/2005 | Pfefferle et al. |
| 9,517,097 B2 * | 12/2016 | Rise .................. A61B 17/8085 |
| 10,058,363 B2 | 8/2018 | Burke et al. |
| 2002/0143336 A1 | 10/2002 | Hearn |
| 2008/0082101 A1 | 4/2008 | Reisberg |
| 2009/0318920 A1 | 12/2009 | Jacobs |
| 2010/0331844 A1 | 12/2010 | Ellis et al. |
| 2013/0079777 A1 | 3/2013 | Mohr et al. |
| 2015/0018830 A1 | 1/2015 | Knoepfle et al. |
| 2016/0317199 A1 | 11/2016 | Hartdegen et al. |
| 2017/0065317 A1 | 3/2017 | Burke et al. |

(Continued)

FOREIGN PATENT DOCUMENTS

| | | |
|---|---|---|
| DE | 20300181 U1 | 5/2003 |
| DE | 102006042277 A1 | 3/2008 |

OTHER PUBLICATIONS

Extended European Search Report including Written Opinion for Application No. EP19177888.5, dated Dec. 12, 2019, pp. 1-10.

*Primary Examiner* — Larry E Waggle, Jr.
(74) *Attorney, Agent, or Firm* — Lerner, David, Littenberg, Krumholz & Mentlik, LLP (57) ABSTRACT

A monolithic rib plate is described. The rib plate comprises multiple first screw orifices located substantially along a first line and connected by first bridges, multiple second screw orifices located laterally on one side of the first line and connected by second bridges, wherein one or more of the second bridges have a smaller cross-section than the first bridges, and third bridges, each connecting one of the second screw orifices with one of the first screw orifices. Also described is a rib plate system comprising the monolithic rib plate and at least one of one or more polyaxial locking screws, a tool for removing the second bridges, a tool for bending the monolithic rib plate, and one or more orifice bridge plates.

13 Claims, 4 Drawing Sheets

(56) References Cited

U.S. PATENT DOCUMENTS

| | | |
|---|---|---|
| 2017/0105775 A1 | 4/2017 | Ricker et al. |
| 2018/0125547 A1* | 5/2018 | Bernstein ............. A61B 17/808 |
| 2018/0344372 A1 | 12/2018 | Madjarov et al. |
| 2018/0368896 A1 | 12/2018 | Powell |

* cited by examiner

RIB PLATE AND RIB PLATE SYSTEM

CROSS-REFERENCE TO RELATED APPLICATIONS

This application claims the benefit of the filing date of European Patent Application No. 19177888.5 filed Jun. 3, 2019, the disclosure of which is hereby incorporated herein by reference.

TECHNICAL FIELD

The present disclosure provides a rib plate and a rib plate system for fixing parts of a fractured rib at a desired distance and orientation relative to each other.

BACKGROUND OF THE INVENTION

US 2017/0065317 A1 describes various bone plates. These bone plates comprise screw orifices connected by bridges. Further prior art can be found in DE 10 2006 042 277 A1, US 2010/331844 A1, US 2013/079777 A1, US 2018/344372 A1 and US 2018/368896 A1.

An underlying object is to provide a rib plate and rib plate system that improve versatility, reliability and handling of a surgical procedure in which the rib plate is attached to parts of a fractured rib for fixing them at a desired distance and orientation relative to each other.

BRIEF SUMMARY OF THE INVENTION

According to a first aspect of the present disclosure, a monolithic rib plate comprises multiple first screw orifices located substantially along a first line and connected by first bridges, multiple second screw orifices located laterally on one side of the first line and connected by second bridges, wherein one or more of the second bridges have a smaller cross-section than the first bridges, and third bridges, each connecting one of the second screw orifices with one of the first screw orifices.

The first line may be a straight line or a curved line. A screw orifice is defined as a structure, such as a circular structure, with a hole, such as a circular hole, therethrough.

The first screw orifices, being located substantially along the first line, may be located with their respective center points either on the first line or offset to the first line. Such offset first screw orifices may be alternatingly arranged on the two sides of the first line along the first line. For example, the first screw orifices may be alternatingly arranged at distances, for example at equal distance, from the first line at opposite sides of the first line.

The first bridges may each extend from one first screw orifice to its closest neighboring first screw orifice. So, two closest neighboring first screw orifices may be directly connected by one or more of the first bridges, such as one first bridge. For example, one end of the first bridge connecting two closest neighboring first screw orifices may extend from the one first screw orifice and the opposite end of that first bridge may extend from the other closest neighboring first screw orifice, for example from sides of the respective first screw orifices facing each other.

The second screw orifices, being located laterally on one side of the first line, may be located with their respective center points on one side of the first line, for example each at equal distances from the first line. The second screw orifices and/or the center points of the second screw orifices may be further away from the first line than the first screw orifices and/or the center points of the first screw orifices.

The second bridges may each extend from one second screw orifice to its closest neighboring second screw orifice. So, two closest neighboring second screw orifices may be directly connected by one or more second bridges, such as one second bridge. For example, one end of the second bridge connecting two neighboring second screw orifices may extend from the one second screw orifice and the opposite end of that second bridge may extend from the other closest neighboring second screw orifice, for example from sides of the respective second screw orifices facing each other. The one or more of the second bridges having a smaller cross-section than the first bridges may each have a cross-section which is smaller than the smallest cross-section of the first bridges. As understood herein, the cross-section may be defined by a cross-sectional area.

The third bridges may each extend from one of the second screw orifices to one of its closest neighboring first screw orifices. So, one of the second screw orifices may be directly connected to its closest neighboring first screw orifice by one or more of the third bridges, such as one third bridge. For example, one end of the third bridge connecting two closest neighboring second and first screw orifices extends from the one second screw orifice and the other opposite end of that third bridge may extend from the closest neighboring first screw orifice, for example from sides of the respective second and first screw orifices facing each other.

The second screw orifices may have a curved cross-section, in particular in a plane that extends perpendicular to the first line. An inner radius of the curved second screw orifices may be between 1 mm and 6 mm. The angle of total curvature, for example in a plane of the cross-section of the second screw orifices and orthogonal to the first line, may be between 45° and 100°.

The one or more second bridges having the smaller cross-section may be more flexible than the first bridges. For example, the one or more second bridges having the smaller cross-section may be more flexible in a direction along a straight line parallel to the first line than the first bridges. Alternatively or additionally, the one or more second bridges having the smaller cross-section may be more flexible in a direction along a straight line orthogonal to the first line than the first bridges.

One or more of the third bridges may be more flexible than the first bridges. For example, the one or more third bridges may be more flexible in a direction along a straight line orthogonal to the first line than the first bridges. Alternatively or additionally, one or more of the third bridges may be more flexible in a direction along a straight line parallel to the first line than the first bridges. For example, each third bridge may be more flexible in one direction along a straight line parallel to the first line than in the opposite direction along the straight line parallel to the first line.

Each screw orifice, such as each second screw orifice, may have a center point. A second line may extend through the center points of two neighboring second screw orifices, and the one or more of the second bridges having a smaller cross-section and connecting the two neighboring second screw orifices may be offset relative to the second line in a direction away from the first line. For example, the ends of the second bridge connecting the two neighboring second screw orifices are offset from the second line in a direction away from the first line. Such an approach may result in an off-center connection and force distribution between neighboring second screw orifices. The one or more of the second bridges having a smaller cross-section may extend from the first line as far as or less than the second screw orifices.

At least the one or more of the second bridges having a smaller cross-section may be concavely shaped on their side facing the first line. At least one of the second bridges may be convexly shaped on its side facing away from the first line. For example, at least the one or more of the second bridges having a smaller cross-section may be arc-shaped, such as V-shaped. Two leg portions may extend from a common point of origin at an angle of less than 180° away from each other to connect with the respective second screw orifices. Each leg portion may extend along a line having an extension that intersects a screw hole in the closest neighboring second screw orifice to the respective leg. For example, the line may intersect a center point of the closest neighboring second screw orifice.

At least one of the second screw orifices may be connected to one of the first screw orifices by one of the third bridges and to another of the first screw orifices by another of the third bridges. The combined cross-section of the two third bridges connecting the second screw orifice to the two first screw orifices may be smaller than the cross-section of the first bridge connecting these two first screw orifices. For example, each second screw orifice may have a center point and an intersection line may extend through the center point orthogonal to the first line. The two third bridges may extend from the second screw orifice symmetrically to the intersection line.

At least one of the third bridges may be concavely shaped on its side facing away from the first line. At least one of the third bridges may be convexly shaped on its side facing towards the first line. For example, at least one of the third bridges is arc-shaped, such as V-shaped. Two leg portions may extend from a common point of origin at an angle of less than 180° to connect to the respective first and second orifice. Each leg portion may extend along a line having an extension that intersects a screw hole in the closest neighboring second screw orifice and a screw hole in the closest neighboring first screw orifice to the respective leg. For example, the line may intersect a center point of the respective closest neighboring screw orifice. The leg portions may be open at an angle between 100° and 140°, and may have the same length and/or the same cross-section.

At least one of the second screw orifices may be located halfway between its closest neighboring two first screw orifices. The second screw orifices may be entirely distanced beyond the first screw orifices from the first line. In other words, the end of each of the second screw orifices closest to the first line is still farther away from the first line than the end of each of the first screw orifices farthest away from the first line.

A greatest distance between two of the third bridges connecting one of the first screw orifices with its closest two second screw orifices may be equal to or less than a shortest distance between the one first screw orifice and the second bridge connecting the closest two second screw orifices. A free space at least partially enclosed by one second bridge and two third bridges may extend a distance in a direction of the first line equal to or less than a distance in a direction orthogonal to the first line.

One or more of the first and second screw orifices may comprise an engagement portion configured to engage a threaded head of a polyaxial locking screw at a selected angular orientation. The engagement portion may be realized as a circumferential ring-shaped lip in the screw hole of the respective screw orifice.

The rib plate may comprise between 2 and 30 first screw orifices, such as any number from 5 to 20. The second screw orifices may be as many or less than the number of first screw orifices, such as one less than the number of first screw orifices.

The first screw orifices and the second screw orifices may define respective central screw axes which are angled to each other. For example, the angle is between 30° and 120°, such as between 45° and 90°. As understood herein, central screw axis may be defined by a straight line intersecting the center point of the respective screw orifice or its screw hole while extending orthogonally therethrough. The screw orifices may be symmetrical about their respective central screw axis. The central screw axes may extend orthogonally to a surface of the bone plate.

According to a second aspect of the present disclosure, a rib plate system comprises the monolithic rib plate and at least one of one or more polyaxial locking screws, a tool for removing the second bridges, a tool for bending the monolithic rib plate, and one or more second screw orifice bridge plates. For example, the bridge plates described below. When polyaxial locking screws are provided, they may engage the respective engagement portion at a maximum engagement angle of up to 15°, such as up to 10°. This maximum engagement angle may be uniform about the respective central screw axis.

According to a third aspect of the present disclosure, a rib plate system comprises a monolithic rib plate and one or more orifice bridge plates, wherein the monolithic rib plate comprises multiple screw orifices of which two or more first screw orifices are located substantially along a first line and connected by first bridges. The bridge plate comprises multiple plate screw orifices connected by plate bridges, wherein the arrangement of at least two plate screw orifices of the bridge plate matches the arrangement of at least two screw orifices of the rib plate, and wherein one or more of the plate bridges have a smaller cross-section than the first bridges.

The arrangement of at least two plate screw orifices of the bridge plate may match the arrangement of at least two screw orifices of the rib plate. This may be realized by the provision of the at least two plate screw orifices of the bridge plate being equally distanced and oriented to each other as the at least two matching screw orifices of the rib plate. For example, the bridge plate may have a pattern of at least two plate screw orifices which matches a pattern of screw orifices of the rib plate when the bridge plate is placed on the rib plate. The greatest single bridge cross-section between the at least two plate screw orifices may be less than the bridge cross-section of the at least two matching screw orifices of the rib plate. The bridge plate may be positioned such on the rib plate that the center points of the at least two plate screw orifices of the bridge plate are concentric with the center points of the at least two screw orifices of the rib plate. Such a matching arrangement allows a local adjustment of the flexibility of the rib plate as desired, since the flexibility between the at least two screw orifices of the rib plate can be decreased by the rib plate being additionally mounted thereto.

The rib plate may comprise second screw orifices each extending from and connected to the first screw orifices by third bridges, for example the third bridges described herein in the context of the first aspect. The arrangement of the at least two plate screw orifices of the bridge plate may match the arrangement of at least two of the second screw orifices of the rib plate. The second screw orifices may further have the properties of the second screw orifices described herein in the context of the first aspect. The one or more plate bridges having the smaller cross-section may have the properties described herein with regard to the second bridges in the context of the first aspect.

At least one of the plate screw orifices may be connected to a neighboring plate screw orifice by two of the second bridges. A space between the two plate bridges may be shaped as a rhombus. A greatest distance between the two plate bridges connecting neighboring plate screw orifices may be equal to or greater than a shortest distance between the two plate screw orifices. Each first screw orifice may be connected by one of the first bridges to its neighboring first screw orifice. The combined cross-section of the two plate bridges may be smaller than the cross-section of one of the first bridges. The cross-section of a plate bridge may be between 50% and 100% of the cross-section of the one of the first bridges. The plate screw orifices may have screw holes with a larger diameter than the screw holes of the lateral and/or first screw orifices.

According to a fourth aspect of the present invention, a monolithic rib plate comprises a multiple first screw orifices located substantially along a first line and connected by first bridges, multiple second screw orifices located laterally on one side of the first line and connected by second bridges, and third bridges, each connecting one of the second screw orifices with one of the first screw orifices. Each second screw orifice has a center point and wherein a second line extends through the center points of two neighboring second screw orifices, one or more of the second bridges have a smaller cross-section than the first bridges, and the one or more of the second bridges having a smaller cross-section and connecting the two neighboring second screw orifices are offset relative to the second line in a direction away from the first line.

BRIEF DESCRIPTION OF THE DRAWINGS

The foregoing summary and the following detailed description of the present disclosure will be better understood when read in conjunction with the appended drawings. In the drawings:

FIG. 8 is a perspective view of a third rib plate having curved screw orifices with or without a bridge in-between.

DETAILED DESCRIPTION

In the drawings, the same reference numerals are used to denote the same or similar features.

Figure 1A:
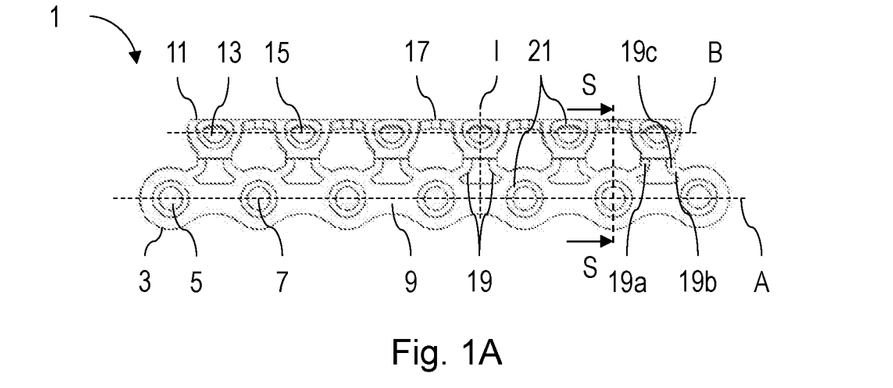
FIG. 1A is a front view of a first rib plate according to an embodiment of the present disclosure, with screw orifices connected by bridges.

FIG. 1A shows a first monolithic rib plate 1 from its front. The monolithic rib plate 1 may be an integral one-piece plate, such as one-piece plate made from a single material (e.g., a metallic material). The rib plate 1 comprises seven planar and circular first screw orifices 3, which each have a circular hole 5 and a center point 7 at their center. The first screw orifices 3 are located along a straight first line A at equal distances and connected by uniform first bridges 9.

The rib plate 1 further has six curved and circular second screw orifices 11, which each have a circular hole 13 and a center point 15 at their center. The second screw orifices 11 are located laterally on one side of the first line A along a straight second line B at equal distances and connected by uniform second bridges 17. The second bridges 17 have a smaller cross-section (i.e., cross-sectional area) than the first bridges 9.

Having a smaller cross-section may in some implementations have the general purpose to improve bending and cutting compared to a greater cross-section. Each reference to a cross-section of a bridge may refer to a cross-section of a portion of the respective bridge. The "smaller" comparison may refer to the smallest cross-section of one bridge being smaller than the smallest cross-section of another bridge.

The rib plate 1 further comprises third bridges 19. Each third bridge 19 connects one of the second screw orifices 11 with one of its closest neighboring first screw orifices 3.

In the embodiment of the first rib plate 1 shown in FIG. 1A, the center points 15 of the second screw orifices 11 are located on a second straight line B parallel to the first straight line A. Here, the second screw orifices 11 are located halfway between their respective closest neighboring two first screw orifices 3. These neighboring two first screw orifices 3 have a distance between their respective center points 7 of 10 mm along the first line A. They are also distanced entirely beyond their closest neighboring two first screw orifices 3 from the first line A.

The third bridges 19 are arc-shaped. Concretely, they substantially have the form of a V. Each of the third bridges 19 has a concave side facing away from the first line A and a convex side facing towards the first line A. The V-shape is constituted by two leg portions 19a, 19b extending from a common point of origin 19c at an angle of 120°. One leg portion 19a extends from the respective second screw orifice 11 orthogonally toward the first line A. In the present embodiment, the leg portions 19a, 19b are equally long and have a uniform cross-section. The second screw orifices 11 are connected to one of the first screw orifices 3 by one of the third bridges 19 and to another of the first screw orifices 3 by another of the third bridges 19. The combined cross-section of the two third bridges 19 connecting the second screw orifice 11 to the two first screw orifices 3 is smaller than the cross-section of the first bridge 9 connecting these two first screw orifices 3. Each second screw orifice 11 has an intersection line I extending through its center point 15 orthogonal to the first line A. The two third bridges 19 extend from the second screw orifice 11 symmetrically to the intersection line I.

The screw orifices 3, 11 comprise an engagement portion 21 in the form of a circumferential ring-shaped lip 21 in their respective hole 5, 13. The engagement portion 21 is configured to engage a threaded head of a polyaxial locking screw at a selected angular orientation as described below with reference to FIG. 1C. The lip 21 has a thickness of approximately 0.15 mm. It extends at an angle of 120° towards the center point 7, 15 of the respective screw orifice 3, 11. The thickness of the rib plate 1 is 1 mm, but could generally range between 0.5 mm and 4 mm.

Figure 1B:
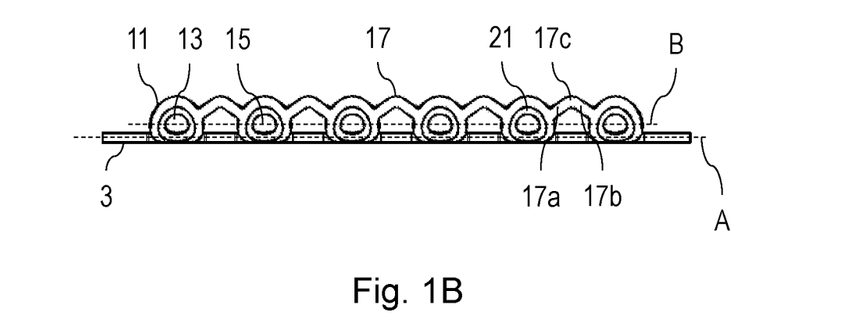
FIG. 1B is a top view of the rib plate in FIG. 1A.

FIG. 1B shows a planar view of the first rib plate 1 to better illustrate the second bridges 17 connecting the second screw orifices 11. As illustrated in FIG. 1B, the second bridges 11 are arc-shaped (substantially in the form of a V). They have a concave side facing towards the first line A and a convex side facing away from the first line A. The V-shape is constituted by two leg portions 17a, 17b extending from a common point of origin 17c at an angle of 120°. Each leg portion 17a, 17b may extend along a uniform line having an extension that intersects the circular hole 13 and/or the center point 15 of the closest neighboring second screw orifice 11 of the respective leg 17a, 17b. In the present embodiment, the legs are equally long and have a uniform cross-section.

Figure 1C:
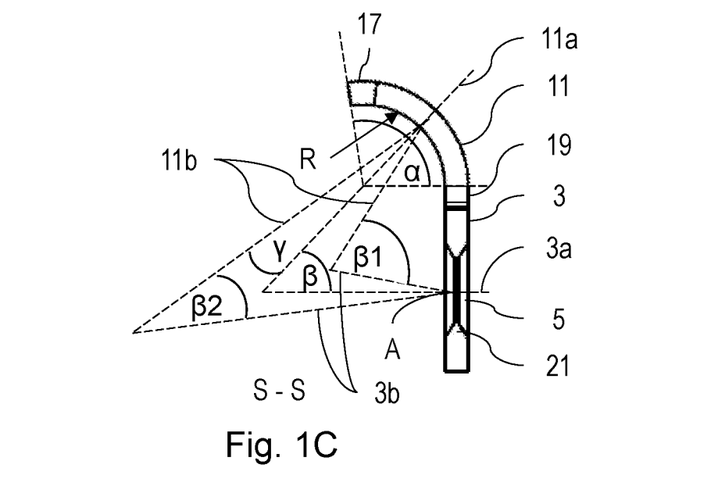
FIG. 1C is a cross-sectional view S-S through the rib plate in FIG. 1A.

FIG. 1C shows a cross-section S-S indicated in FIG. 1A through the rib plate 1 to better illustrate the curved second screw orifices 11. As shown, the second screw orifices 11 are curved in a plane that extends perpendicular to the first line A. An inner uniform radius R of the curved second screw orifices 11 may be between 1 mm and 6 mm (e.g., between 2 mm and 5 mm, such as between 3 mm and 4 mm). An angle of total curvature a of the second screw orifices 11 in the plane of curvature may be between 45° and 110° (e.g., between 90 and 100°). The first screw orifices 3 and the second screw orifices 11 define respective central screw axes 3a, 11a about which the first screw orifices 3 and the second screw orifices 11 are symmetrical, wherein the central screw axes 3a, 11a extend orthogonally to a surface of the bone plate 1, i.e., along an axis normal to a surface of the bone plate 1. The central screw axes 3a, 11a viewed from the side of the rib plate 1—in the direction of the first line A—are inclined to each other at an inclination angle β of between approximately or exactly 30° and 120°, between 45° and 90°, between 45° and 50°, or here 49°.

A polyaxial screw can be engaged with the engagement portion 21 of the respective first screw orifice 3 and/or the respective second screw orifice 11 at a maximum engagement angle γ of up to approximately or exactly 15°, 12°, or 10° from the respective central screw axes 3a, 11a, resulting in a cone shaped engagement zone with its tip in the center of the respective screw orifices 3, 11 and on their respective central screw axes 3a, 11a. The outer surface of this cone shape shaped engagement zone is defined in FIG. 1C by respectively angled screw axes 3b, 11b which are angled relative to the respective central screw axes 3a, 11a at the maximum angle in opposite directions from the respective central screw axes 3a, 11a. Thus, when viewed form the side of the rib plate 1, the angled screw axes 3b, 11b overlap each other at a maximum angle β1 (β+2×γ) and at a minimum angle β2 (β−2×γ). Thereby, a small angle of deviation from the central screw axes 3a, 11a of 10°, for example, leads to a large angular range, here 40°, between the maximum angle β1, here 69°, and the minimum angle β2, here 29°, for adjusting polyaxial screws to the available rib bone material. Thereby, neighboring screws can be angled not only toward each other but also away from each other in different planes and directions, allowing the surgeon to achieve a stronger, more reliable connection between the rib plate 1 and an underlying rib.

Figure 2:
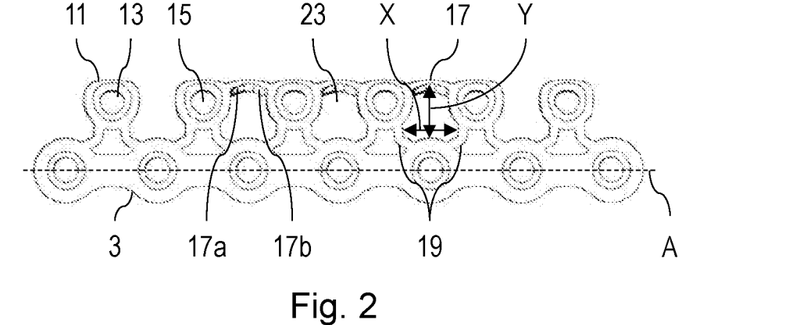
FIG. 2 is a front view of the rib plate in FIG. 1A with two bridges being removed.

FIG. 2 shows the rib plate 1 in which the outermost second bridges 17 have been removed. This can be done either during or prior to surgery to locally adjust the flexibility of the rib plate 1, i.e., increasing the flexibility by removing bridges in general. The removal of a second bridge 17 can be performed by inserting a tool for removing the second bridges between two neighboring second screw orifices 11. Then the second screw bridge 17 therebetween are cut to disconnect its two legs 17a, 17b, remove the second bridge 17 partially or remove the second bridge 17 entirely—the latter of which is shown here.

A greatest distance X between two of the third bridges 19 connecting one of the first screw orifices 3 with its closest two second screw orifices 11 is less than a shortest distance Y between the one first screw orifice 3 and the second bridge 17 connecting the closest two second screw orifices 11. A free space 23 enclosed by one second bridge 17 and two third bridges 3 extends a distance X in a direction of the first line A equal to or less than a distance Y in a direction orthogonal to the first line A. By removing a second bridge 17 the respective neighboring second screw orifices 11 become more flexible.

Figure 3:
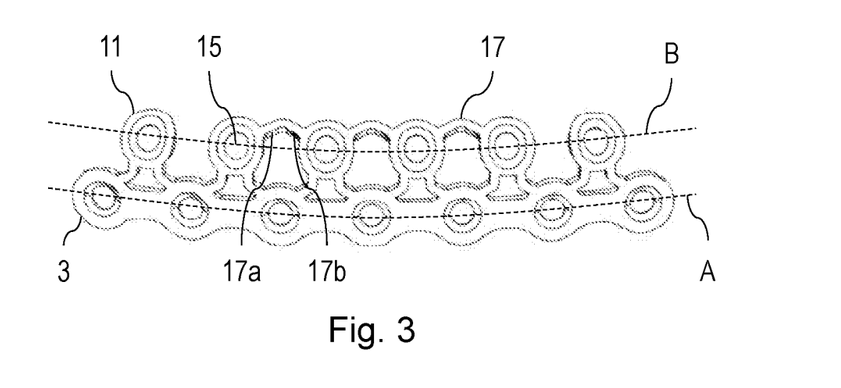
FIG. 3 is a front view of the rib plate in FIG. 2 being bent.

FIG. 3 shows the rib plate 1 of FIG. 2, which has been bent such that the first screw orifices 3 are now located along a curved first line A. This can be performed by a bending tool prior to or during surgery to adjust the rib plate 1 to parts of a fractured rib. Such bending into an anatomical curvature is simplified not only by a possible prior removal of second bridges 17 but also by the arrangement of the second bridges 17 that remain on the rib plate 1. The ends of the second bridge 17 connecting two neighboring second screw orifices 11 are offset from the second line B, which here uniformly extends through the center points 15 of the two neighboring second screw orifices 11, in a direction away from the first line A. As shown, the second bridges 17 extend from the first line A as far as the second screw orifices 11.

Figure 4:
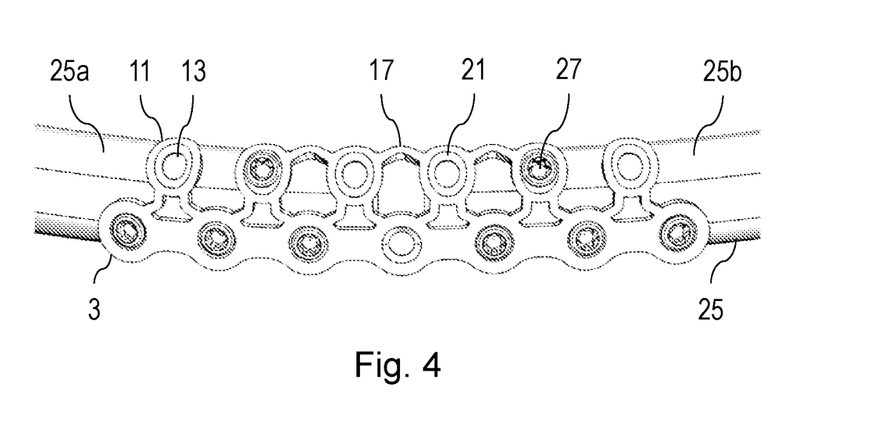
FIG. 4 is a front view of the rib plate in FIG. 3 fixing two parts of a fractured rib at a desired distance and orientation by means of screws engaging with the screw orifices.

FIG. 4 shows the rib plate 1 of FIG. 3 fixing two parts 25a, 25b of a fractured rib 25 at a desired distance and orientation relative to each other by means of screws 27 engaging with the respective engagement portion 21 of the holes 5, 13 of respective screw orifices 3, 11. For this purpose polyaxial locking screws 27 with a threaded head (not shown) are used. As illustrated in FIG. 4, only some of the screw orifices 3, 11 may be fixed to the respective fractures rib parts 25a, 25b in order to adjust the flexibility of the rib plate 1 on the fractured rib 25.

Figure 5:
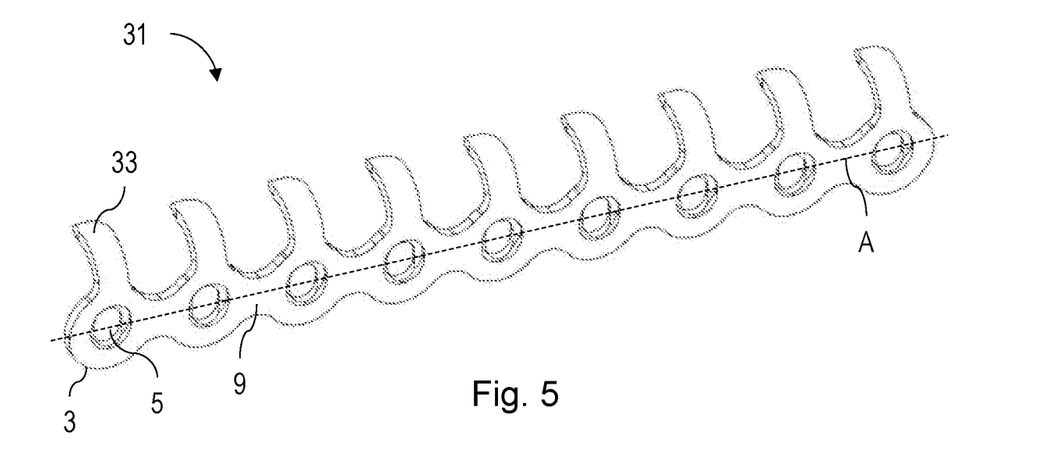
FIG. 5 is a perspective view of a second rib plate having curved hooks extending from first screw orifices.

FIG. 5 shows a perspective view of a second monolithic rib plate 31 which differs from the first rib plate 1 by lacking second screw orifices, second bridges and third bridges. Instead, the second rib plate 31 has curved hooks 33 extending from the first screw orifices 3 along a plane, which is orthogonal to the first line A and intersects the center points 5 of the respective first screw orifices 3. The angle of total curvature of the hooks 33 corresponds to the angle of total curvature of the second screw orifices 11 of the first rib plate 1.

Figure 6:
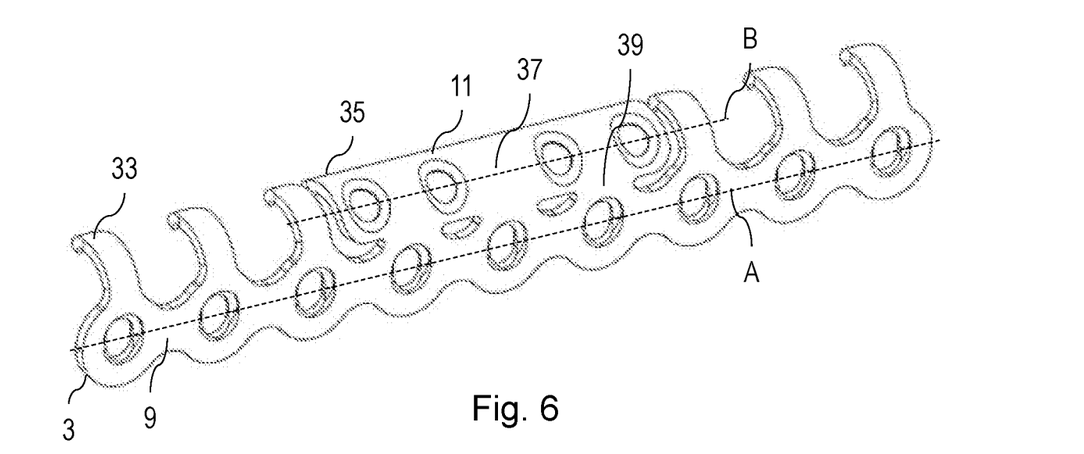
FIG. 6 is a perspective view of a modification of the second rib plate in FIG. 5 having a second screw orifice portion in-between the hooks.

FIG. 6 shows a modification of the second rib plate 31 of FIG. 5. The modification has additionally to the curved hooks 33 extending from the first screw orifices 3 a uniform single hook portion 35 in-between hooks 33 and located in the center of the rib plate 31. The hook portion 35 is wider than the hooks 33 in the direction of the first line A. The hook portion 35 comprises second screw orifices 11, which are symmetrically arranged with regard to a central plane of the hook portion 35 extending orthogonally to the first line A. The second screw orifices 11 are located along a second line B parallel to the first line A. The portions of the hook portion 35 between two second screw orifices 11 may also be referred to as second bridges 37. Multiple third bridge portions 39 connect the hook portion 35 with multiple first screw orifices 3. The third bridges 39 are as flexible as the first bridges 9 but less flexible than the second bridges 37.

Figure 7:
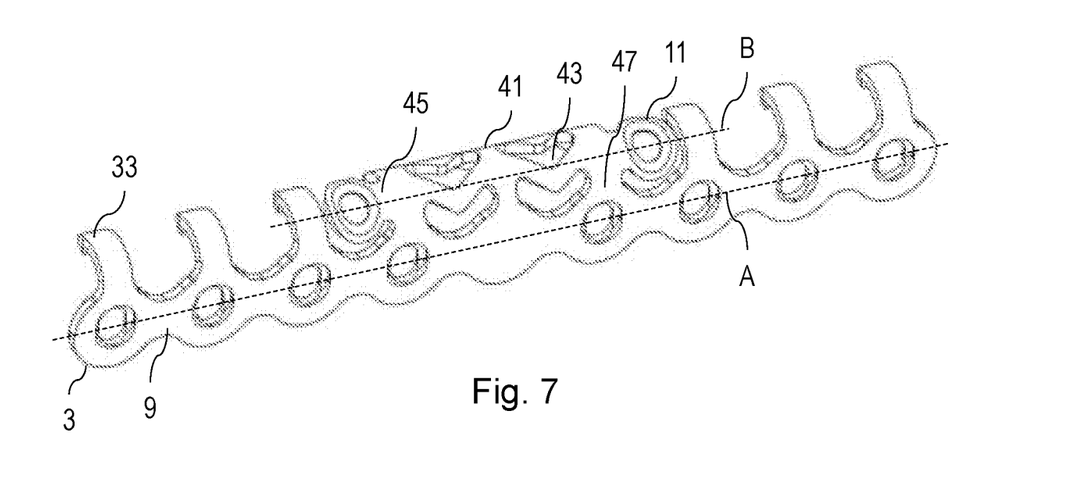
FIG. 7 is a perspective view of another modification of the second rib plate in FIG. 5 having another second screw orifice portion in between the hooks.

FIG. 7 shows another modification of the second rib plate 31 of FIG. 5. The modification differs from the modification in FIG. 6 by a single hook portion 41 which now comprises cutouts 43 and one second screw orifice 11 on each end of the hook portion 41 along the second line B connected by second bridges 45 to the central hook portion 41. The central hook portion 41 is connected to multiple first screw orifices 3 by third bridges 47. The third bridges 47 are as flexible as the first bridges 9 but less flexible than the second bridges 45.

Figure 8:
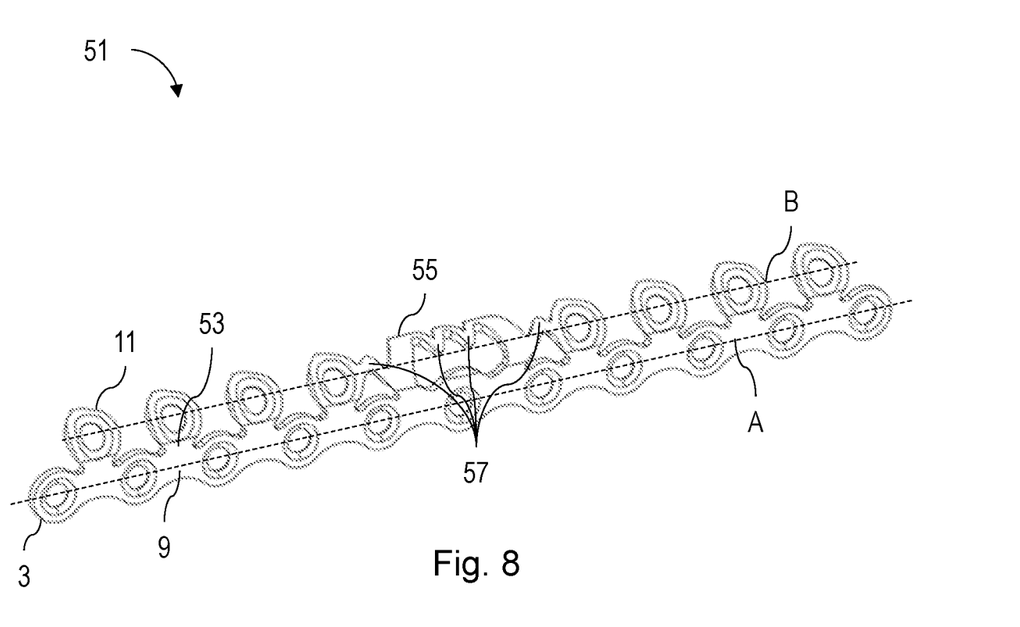

FIG. 8 shows a third monolithic rib plate 51 comprising the curved second screw orifices 11 of the first plate 1 each connected by one of the third bridges 53 to a respective center of a first bridge 9. Thereby, each of the second screw orifices 11 is connected to its closest neighboring first screw orifices 3 via one of the third bridges 53 and one of the first bridges 9. In the center of the rib plate 51 a single second bridge portion 55 connects the two neighboring central second screw orifices 11 with each other. The second bridge portion 55 also connects these two central screw orifices 11 with two of the first bridges 9 of three first screw orifices 3 located in-between along the first line A. The second bridge portion 55 comprises multiple V-shape portions 57 in its extension between the two neighboring central second screw orifices 11.

Figure 9:
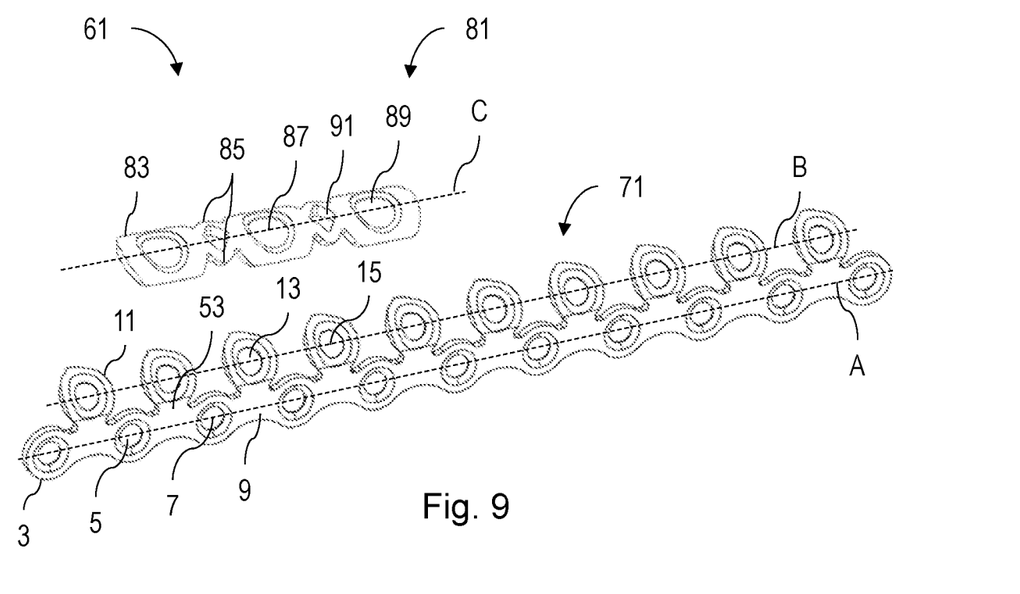
FIG. 9 is a perspective view of a rib plate system with a fourth rib plate having curved screw orifices and a screw orifice bridge plate for further reinforcement in-between neighboring screw orifices.

FIG. 9 shows a rib plate system 61. The rib plate system 61 comprises a fourth monolithic rib plate 71 and an orifice bridge plate 81. Instead of the fourth monolithic rib plate 71, the system 61 may comprise any of the other aforementioned rib plates 1, 31, 51 as well as their respective modifications.

The fourth rib plate 71 comprises multiple screw orifices 3, 11. More than two of the first screw orifices 3 are located substantially along a first line A and connected by first bridges 9, just like in the first rib plate 1 shown in FIG. 1A. The rib plate 71 further comprises second screw orifices 11 along the second line B. The second screw orifices 11 extend from and are connected to the first screw orifices 3 by single third bridges 53, just like in the third rib plate 51 shown in FIG. 8. Alternatively, the second screw orifices 11 may be connected to the first screw orifices 3 by the third bridges 19 described above in the context of the first rib plate 1. The second screw orifices 11 may further have the properties of the second screw orifices described above in the context of the first rib plate 1. For example, they may be connected by the second bridges 17 of the first plate 1. These second bridges 17 may have the properties described above in the context of the first rib plate 1.

The bridge plate 81 comprises multiple plate screw orifices 83 along a plate line C and connected by plate bridges 85. The arrangement of at least two of the plate screw orifices 83 of the bridge plate 81 matches the arrangement of at least two of the screw orifices 3, 11 of the rib plate 71. Center points 87 of respective circular holes 89 of the at least two of the plate screw orifices 83 of the bridge plate 81 are matching the center points 7, 15 of the at least two screw orifices 3, 11 of the rib plate 71. For example, the matching is realized by the center points 87 of the respective circular holes 89 of the at least two of the plate screw orifices 83 of the bridge plate 81 being concentric with the center points 7, 15 of the at least two screw orifices 3, 11 of the rib plate 71, when the bridge plate 81 is placed on the rib plate 71. The greatest single plate bridge 85 cross-section between the at least two plate screw orifices 83 is less than the smallest first bridge cross-section of the at least two matching screw orifices 3, 11 of the rib plate 71. The arrangement of the at least two plate screw orifices 83 of the bridge plate 81 may match the arrangement of at least two second screw orifices 11 of the rib plate 71. The number of plate screw orifices may be from 2 to 10, such as 3 to 7. Here, the number of plate screw orifices is three, which offers a variety of applications at a minimum size of the bridge plate 81. For example, one plate screw orifice 83 can be removed from the other two, if necessary. Also, screws 27 can be placed in only two or all of the three plate screw orifices 83 for an individual adjustment of the flexibility of the rib plate system 61 in a state attached to parts 25a, 25b of a fractured rib 25.

In this case, a plate screw orifice 83 is connected to a neighboring plate screw orifice 83 by two second bridges 85. A space 91 between the two second bridges 85 is shaped as a rhombus. A greatest distance between the two plate bridges 85 connecting neighboring plate screw orifices 83 is greater than a shortest distance between the two plate screw orifices 83. A first screw orifice 3 is connected by one first bridge 9 to its neighboring first screw orifice 3. The combined cross-section of the two plate bridges 85 is smaller than the cross-section of the first bridges 9. The cross-section of a single plate bridge 85 is between 50% and 100% of the cross-section of the first bridges 9. The plate screw orifices 83 may have holes 89 with a larger diameter than the holes 13, 5 of the second and/or first screw orifices 11, 3.

The disclosure also provides a surgical technique of applying a rib plate 1, 31, 51, 71 to parts 25a, 25b of a fractures rib 25. This technique includes the step of cutting or more second bridges 17 and/or third bridges 19 to adjust the flexibility in a portion of the rib plate 1, 31, 51, 71. The technique also includes bending the rib plate 1, 31, 51, 71 in a lateral direction to adjust the rib plate 1, 31, 51, 71 to the curvature of the fractured rib 25, and attaching the rib plate 1, 31, 51, 71 with screws 27 engaging only some or all of the screw orifices 3, 11.

The technique may include the step of bending the rib plate 1, 31, 51, 71 in at least two planes orthogonal to each other to even better adjust the rib plate 1, 31, 51, 71 to parts 25a, 25b of the fractured rib 25. Also provided may be the step of attaching the rib plate 1, 31, 51, 71 with screws 27 engaging the screw orifices 3, 11 symmetrically to a central cross-sectional plane through the rib plate rib plate 1, 31, 51, 71 orthogonal to the first line A. Further, the step of attaching may be limited to attaching the rib plate 1, 31, 51, 71 with screws 27 engaging only those of the second screw orifices 11 still comprising a second bridge 17 connecting them to a neighboring second screw orifice 11. Optionally, the step of attaching may require that all of the screw orifices 3, 11 can serve for the engagement of a screw but the central one or two screw orifices, which remain screw-free after surgery.

It should be understood that the invention is not limited to the specific embodiments disclosed above and only limited by the scope of the claims that follow.

The invention claimed is:
1. A monolithic rib plate, comprising:
multiple first screw orifices located substantially along a first line and connected by first bridges;
multiple second screw orifices located laterally on one side of the first line and connected by second bridges, wherein one or more of the second bridges have a smaller cross-section than the first bridges; and third bridges, each connecting one of the second screw orifices with one of the first screw orifices, wherein at least one of the second screw orifices is located halfway between its closest two first screw orifices.

2. The monolithic rib plate according to claim 1, wherein the second screw orifices each have a curved cross-section.

3. The monolithic rib plate according to claim 1, wherein the one or more second bridges having the smaller cross-section are more flexible than the first bridges.

4. The monolithic rib plate according to claim 1, wherein one or more of the third bridges are more flexible than the first bridges.

5. The monolithic rib plate according to claim 1, wherein each second screw orifice has a center point and wherein a second line extends through the center points of two neighboring second screw orifices, and wherein the one or more of the second bridges having the smaller cross-section and connecting the two neighboring second screw orifices are offset relative to the second line in a direction away from the first line.

6. The monolithic rib plate according to claim 1, wherein at least the one or more of the second bridges having the smaller cross-section are concavely shaped on their side facing the first line.

7. The monolithic rib plate according to claim 1, wherein at least one of the third bridges is concavely shaped on its side facing away from the first line.

8. The monolithic rib plate according to claim 1, wherein one or more of the first and second screw orifices comprises an engagement portion configured to engage a threaded head of a polyaxial locking screw at a selected angular orientation.

9. The monolithic rib plate according to claim 1, wherein the first screw orifices and the second screw orifices define respective central screw axes which are angled to each other.

10. A monolithic rib plate, comprising:
multiple first screw orifices located substantially along a first line and connected by first bridges;
multiple second screw orifices located laterally on one side of the first line and connected by second bridges, wherein one or more of the second bridges have a smaller cross-section than the first bridges; and
third bridges, each connecting one of the second screw orifices with one of the first screw orifices,
wherein at least one of the second screw orifices is connected to one of the first screw orifices by one of the third bridges and to another of the first screw orifices by another of the third bridges.

11. The monolithic rib plate according to claim 10, wherein a combined cross-section of the two third bridges connecting the second screw orifice to the two first screw orifices is smaller than the cross-section of the first bridge connecting these two first screw orifices.

12. A monolithic rib plate, comprising:
multiple first screw orifices located substantially along a first line and connected by first bridges;
multiple second screw orifices located laterally on one side of the first line and connected by second bridges, wherein one or more of the second bridges have a smaller cross-section than the first bridges; and
third bridges, each connecting one of the second screw orifices with one of the first screw orifices,
wherein a greatest distance between two of the third bridges connecting one of the first screw orifices with its closest two second screw orifices is equal to or less than a shortest distance between the one first screw orifice and the second bridge connecting the closest two second screw orifices.

13. A monolithic rib plate, comprising:
multiple first screw orifices located substantially along a first line and connected by first bridges;
multiple second screw orifices located laterally on one side of the first line and connected by second bridges, wherein one or more of the second bridges have a smaller cross-section than the first bridges; and
third bridges, each connecting one of the second screw orifices with one of the first screw orifices,
wherein a free space at least partially enclosed by one second bridge and two third bridges extends a distance in a direction of the first line equal to or less than a distance in a direction orthogonal to the first line.

* * * * *